US006638482B1

(12) United States Patent
Ackley et al.

(10) Patent No.: US 6,638,482 B1
(45) Date of Patent: *Oct. 28, 2003

(54) RECONFIGURABLE DETECTION AND ANALYSIS APPARATUS AND METHOD

(75) Inventors: Donald E. Ackley, Cardiff, CA (US); Edward L. Sheldon, San Diego, CA (US); Michael K. Krihak, San Diego, CA (US)

(73) Assignee: Nanogen, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/204,324

(22) Filed: Dec. 2, 1998

Related U.S. Application Data

(63) Continuation-in-part of application No. 08/753,962, filed on Dec. 4, 1996, now Pat. No. 6,287,517, and a continuation-in-part of application No. 08/709,358, filed on Sep. 6, 1996, now Pat. No. 6,129,828, which is a continuation-in-part of application No. 08/534,454, filed on Sep. 27, 1995, now Pat. No. 5,849,486, which is a continuation-in-part of application No. 08/304,657, filed on Sep. 9, 1994, now Pat. No. 5,632,957, which is a continuation-in-part of application No. 08/271,882, filed on Jul. 7, 1994, now Pat. No. 6,017,696, which is a continuation-in-part of application No. 08/146,504, filed on Nov. 1, 1993, now Pat. No. 5,605,662.

(51) Int. Cl.$^7$ .............. G01N 15/00; G01N 1/00; B01J 8/00; C12Q 1/68; C12P 19/34

(52) U.S. Cl. .............. 422/68.1; 422/50; 422/129; 435/6; 435/7; 435/91.1

(58) Field of Search .............. 422/50, 68.1, 129; 435/6, 7.1, 91.1

(56) References Cited

U.S. PATENT DOCUMENTS

| 3,950,738 A | 4/1976 | Hayashi et al. ....... 340/173 LS |
| 3,995,190 A | 11/1976 | Salgo ............... 313/391 |

(List continued on next page.)

FOREIGN PATENT DOCUMENTS

| EP | 0228075 | 7/1987 |
| GB | 2156074 | 10/1985 |

(List continued on next page.)

OTHER PUBLICATIONS

Sato et al., *Individual and Mass Operation of Biological Cells Using Micromechanical Silicon Devices*, Central Research Laboratory, Advanced Research Laboratory, Hitachi, Ltd., 1–29– Higshikoigakubo, Kokubunji, Tokyo 185 Japan; Sensors and Actuators, A21 A23 (1990) pp. 948–953.

(List continued on next page.)

*Primary Examiner*—Ardin H. Marschel
(74) *Attorney, Agent, or Firm*—O'Melveny & Myers LLP

(57) ABSTRACT

Methods and apparatus for use of a stacked, reconfigurable system is provided. The stacked, reconfigurable system includes an inlet for receipt of a sample, a first chamber defined by a bottom support, an intermediate member, and a first spacer, the first chamber being coupled to the inlet through the bottom support, the first chamber including an analysis system having electrodes for electrophoretic transport of material. A second chamber is stacked on top of the first chamber, the second chamber being defined by the intermediate member, a top member, and a second spacer, the second chamber being in fluid communication with the first chamber through at least one via formed in the intermediate member, the second chamber being electrically reconfigurable to permit action such as, for example, synthesis of a compound or specialized analysis. The apparatus can be used to perform analysis on charged biological materials.

9 Claims, 5 Drawing Sheets

U.S. PATENT DOCUMENTS

| | | | |
|---|---|---|---|
| 4,563,419 A | 1/1986 | Ranki et al. | 435/6 |
| 4,580,895 A | 4/1986 | Patel | 356/39 |
| 4,584,075 A | 4/1986 | Goldstein et al. | 204/182.3 |
| 4,594,135 A | 6/1986 | Goldstein | 204/180.1 |
| 4,751,177 A | 6/1988 | Stabinsky | 435/6 |
| 4,787,963 A | 11/1988 | MacConnell | 204/180.1 |
| 4,816,418 A | 3/1989 | Mack et al. | 436/518 |
| 4,822,566 A | 4/1989 | Newman | 422/68 |
| 4,908,112 A | 3/1990 | Pace | 204/299 |
| 5,063,081 A | 11/1991 | Cozzette et al. | 427/2 |
| 5,075,077 A | 12/1991 | Durley, III et al. | 422/56 |
| 5,096,807 A | 3/1992 | Leaback | 435/6 |
| 5,125,748 A | 6/1992 | Bjornson et al. | 356/414 |
| 5,126,022 A | 6/1992 | Soane et al. | 204/180.1 |
| 5,143,854 A | 9/1992 | Pirrung et al. | 436/518 |
| 5,164,319 A | 11/1992 | Hafeman et al. | 435/291 |
| 5,166,063 A | 11/1992 | Johnson | 435/173 |
| 5,200,051 A | 4/1993 | Cozzette et al. | 204/403 |
| 5,202,231 A | 4/1993 | Drmanec et al. | 435/6 |
| 5,219,726 A | 6/1993 | Evans | 435/6 |
| 5,227,265 A | 7/1993 | DeBoer et al. | 430/41 |
| 5,234,566 A | 8/1993 | Osman et al. | 204/403 |
| 5,304,487 A | 4/1994 | Wilding et al. | 435/291 |
| 5,312,527 A | 5/1994 | Mikkelsen et al. | 204/153.12 |
| 5,393,401 A | 2/1995 | Knoll | 204/418 |
| 5,434,049 A | 7/1995 | Okano et al. | 435/6 |
| 5,654,136 A * | 8/1997 | Sasaki et al. | 435/5 |
| 5,922,591 A * | 7/1999 | Anderson et al. | 435/287.2 |
| 6,007,690 A | 12/1999 | Nelson et al. | 204/601 |

FOREIGN PATENT DOCUMENTS

| | | |
|---|---|---|
| JP | 05317030 | 3/1993 |
| WO | 8603782 | 7/1986 |
| WO | WO88/08528 | 11/1988 |
| WO | WO89/01159 | 2/1989 |
| WO | 8910977 | 11/1989 |
| WO | 9001564 | 2/1990 |
| WO | WO92/044770 | 3/1992 |
| WO | WO93/22678 | 11/1993 |
| WO | WO95/01159 | 1/1995 |
| WO | WO95/07363 | 3/1995 |
| WO | WO96/07917 | 3/1996 |
| WO | WO96/14509 | 5/1996 |
| YU | 57087 | 4/1987 |

OTHER PUBLICATIONS

Anand and Southern "Pulsed Field Gel Electrophoresis," *Gel Electrophoresis of Nucleic Acids—A Practical Approach*, 2d. Ed., D. Rickwood and B.D. Hames (New York:IRL Press 1990), pp 101–123.

Anderson and Young, "Quantitative Filter Hybridization," *Nucleic Acid Hybridization—A Practical Approach*, Eds. B.D. Hames and S.J. Higgins (Washington, D.C. :IRL Press 1985) pp 73–111.

Baines, "Setting a Sequence to Sequence a Sequence," *Bio/Technology*, 10:757–758 (1992).

Barinaga, "Will 'DNA Chip' Speed Genome Initiative?", *Science*, 253:1489 (1991).

Beattie et al., "Genosensor Technology," *The 1992 San Diego Conference: Genetic Recognition*, pp 1–5 (Nov., 1992).

Beltz et al., "Isolation of Multigene Families and Determination of Homologies by Filter Hybridization Methods," *Methods in Enzymology*, 100:266–285 (1983).

Connor et al., "Detection of Sickle Cell $\beta^3$–Globin Allele by Hybridization With Synthetic Oligonucleotides," *Proc. Natl. Acad. Sci. USA*, 80:278–282 (1983).

Drmanac et al., "Sequencing of Megabase Plus DNA by Hybridization: Theory of the Method," *Genomics*, 4:114–128 (1989).

Drmanac et al., "DNA Sequence Determination by Hybridixation: A Strategy for Efficeint Large–Scale Sequencing," *Science*, 260: 1649–1652 (1993).

Fodor et al., "Multiplexed Biochemical Assays With Biological Chips," *Nature*, 364:555–556 (1993).

Fodor et al., "Light–Directed, Spatially Addressable Parallel Chemical Synthesis," *Science*, 251:767–773 (1992).

Horejsi, "Some Theoretical Aspects of Affinity Electrophoresis," *Journal of Chromatography*, 178:1–13 (1979).

Horjsi et al., Determination of Dissociation Constants of Lectin Sugar Complexes by Means of Affinity Electrophoresis, *Biochimica at Biophysica Acta*, 499:200–300 (1977).

Ranki et al., "Sandwich Hybridization as a Convenient Method for the Detection of Nucleic Acids in Crude Samples," *Gene*, 21:77–85 (1983).

Saiki, "Amplification of Genomic DNA," *PCR Protocols: A Guide to Methods and Applications*, (Academic Press, Inc. 1990), pp 13–20.

Southern et al., "Analyzing and Comparing Nucleic Acid Sequences by Hybridization to Arrays of Oligonucleotides Evaluation Using Experimental Models," *Genomics*, 13:1008–1017 (1992).

Strezoska et al., "DNA Sequencing by Hybridization: 100 Bases Read by a Non–Gel–Based Method", *Proc. Natl. Acad. Sci. USA*, 88:10089–93 (1991).

Wallace et al., "Hybridization of Synthetic Oligodcoxyribonucleotides to $\Phi \times 174$ DNA: The Effect of Single Base Pair Mismatch," *Nucleic Acid Res.*, 6:3543–3557 (1979).

Washizu, "Electrostatic Manipulatiaon of Biological Objects," *Journal of Electrostatics*, 25:109–123 (1990).

Washizu and Kurosawa, "Electrostatic Manipulation of DNA in Microfabricated Structures," *IEEE Transactions on Industry Applications*, 26:1165–1172 (1990).

Brown et al., "Electrochemically Induced Adsorption of Radio–Labelled DNA on Gold and HOPG Substrates for STM Investigations", *Ultramicroscopy*, 38 (1991) pp 253–264.

Palacek, "New Trends in Electrochemical Analysis of Nucleic Acids", *Bioelectrochemistry and Bioenergetics*, 20 (1988) pp 179–194.

"Flexcon '96" Technical Society Program.

* cited by examiner

RECONFIGURABLE DETECTION AND ANALYSIS APPARATUS AND METHOD

RELATED APPLICATION INFORMATION

This application is a continuation-in-part application of application Ser. No. 08/753,962, filed Dec. 4, 1996, entitled "Laminated Assembly for Active Bioelectronic Devices", now U.S. Pat. No. 6,287,517, which is a continuation-in-part application of Ser. No. 08/534,454, filed Sep. 27, 1995, entitled "Apparatus and Methods for Active Programmable Matrix Devices", now issued as U.S. Pat. No. 5,849,486, which is a continuation-in-part of application Ser. No. 08/304,657, filed Sep. 9, 1994, entitled, as amended, "Molecular Biological Diagnostic Systems Including Electrodes", now issued as U.S. Pat. No. 5,632,957, which is a continuation-in-part of application Ser. No. 08/271,882, filed Jul. 7, 1994, entitled, as amended, "Methods for Electronic Stringency Control for Molecular Biological Analysis and Diagnostics", now issued as U.S. Pat. No. 6,017,696, which is a continuation-in-part of application Ser. No. 08/146,504, filed Nov. 1, 1993, entitled, as amended, "Active Programmable Electronic Devices for Molecular Biological Analysis and Diagnostics", now issued as U.S. Pat. No. 5,605,662, and application Ser. No. 08/709,358, filed Sep. 6, 1996, entitled "Apparatus and Methods for Active Biological Sample Preparation", now issued as U.S. Pat. No. 6,129,828, all incorporated herein by reference as if fully set forth herein.

FIELD OF THE INVENTION

This invention relates generally to electronic devices for the movement of charged materials, especially charged biological materials. More particularly, it relates to microfluidic systems for the transport and/or analysis of electrically charged materials, especially biological materials including nucleic acids and biological pathogens or toxins.

This application is related to the following applications filed on even date herewith, entitled "Stacked, Reconfigurable System for Electrophoretic Transport of Charged Materials", "Electrophoretic Buss for Transport of Charged Materials in a Multi-Chamber System", and "System Including Functionally Separated Regions in Electrophoretic System".

BACKGROUND OF THE INVENTION

Molecular biology comprises a wide variety of techniques for the analysis of nucleic acid and protein. Many of these techniques and procedures form the basis of clinical diagnostic assays and tests. These techniques include nucleic acid hybridization analysis, restriction enzyme analysis, genetic sequence analysis, and the separation and purification of nucleic acids and proteins (See, e.g., J. Sambrook, E. F. Fritsch, and T. Maniatis, *Molecular Cloning: A Laboratory Manual,* 2 Ed., Cold spring Harbor Laboratory Press, Cold Spring Harbor, N.Y., 1989).

Most of these techniques involve carrying out numerous operations (e.g., pipetting, centrifugations, electrophoresis) on a large number of samples. They are often complex and time consuming, and generally require a high degree of accuracy. Many a technique is limited in its application by a lack of sensitivity, specificity, or reproducibility. For example, these problems have limited many diagnostic applications of nucleic acid hybridization analysis.

The complete process for carrying out a DNA hybridization analysis for a genetic or infectious disease is very involved. Broadly speaking, the complete process may be divided into a number of steps and substeps. In the case of genetic disease diagnosis, the first step involves obtaining the sample (blood or tissue). Depending on the type of sample, various pre-treatments would be carried out. The second step involves disrupting or lysing the cells, which then release the crude DNA material along with other cellular constituents. Generally, several sub-steps are necessary to remove cell debris and to purify further the crude DNA. At this point several options exist for further processing and analysis. One option involves denaturing the purified sample DNA and carrying out a direct hybridization analysis in one of many formats (dot blot, microbead, microplate, etc.). A second option, called Southern blot hybridization, involves cleaving the DNA with restriction enzymes, separating the DNA fragments on an electrophoretic gel, blotting to a membrane filter, and then hybridizing the blot with specific DNA probe sequences. This procedure effectively reduces the complexity of the genomic DNA sample, and thereby helps to improve the hybridization specificity and sensitivity. Unfortunately, this procedure is long and arduous. A third option is to carry out the polymerase chain reaction (PCR) or other amplification procedure. The PCR procedure amplifies (increases) the number of target DNA sequences relative to non-target sequences. Amplification of target DNA helps to overcome problems related to complexity and sensitivity in genomic DNA analysis. All these procedures are time consuming, relatively complicated, and add significantly to the cost of a diagnostic test. After these sample preparation and DNA processing steps, the actual hybridization reaction is performed. Finally, detection and data analysis convert the hybridization event into an analytical result.

The steps of sample preparation and processing have typically been performed separate and apart from the other main steps of hybridization and detection and analysis. Indeed, the various substeps comprising sample preparation and DNA processing have often been performed as a discrete operation separate and apart from the other substeps. Considering these substeps in more detail, samples have been obtained through any number of means, such as obtaining of full blood, tissue, or other biological fluid samples. In the case of blood, the sample is processed to remove red blood cells and retain the desired nucleated (white) cells. This process is usually carried out by density gradient centrifugation. Cell disruption or lysis is then carried out on the nucleated cells to release DNA, preferably by the technique of sonication, freeze/thawing, or by addition of lysing reagents. Crude DNA is then separated from the cellular debris by a centrifugation step. Prior to hybridization, double-stranded DNA is denatured into single-stranded form. Denaturation of the double-stranded DNA has generally been performed by the techniques involving heating (>Tm), changing salt concentration, addition of base (NaOH), or denaturing reagents (urea, formamide, etc.). Workers have suggested denaturing DNA into its single-stranded form in an electrochemical cell. The theory is stated to be that there is electron transfer to the DNA at the interface of an electrode, which effectively weakens the double-stranded structure and results in separation of the strands. See, generally, Stanley, "DNA Denaturation by an Electric Potential", U.K. patent application 2,247,889 published Mar. 18, 1992.

Nucleic acid hybridization analysis generally involves the detection of a very small number of specific target nucleic acids (DNA or RNA) with an excess of probe DNA, among a relatively large amount of complex non-target nucleic acids. The substeps of DNA complexity reduction in sample preparation have been utilized to help detect low copy numbers (i.e. 10,000 to 100,000) of nucleic acid targets. DNA complexity is overcome to some degree by amplification of target nucleic acid sequences using polymerase chain reaction (PCR). (See, M. A. Innis et al, *PCR Protocols: A Guide to Methods and Applications*, Academic Press, 1990). While amplification results in an enormous number of target nucleic acid sequences that improves the subsequent direct probe hybridization step, amplification involves lengthy and cumbersome procedures that typically must be performed on a stand alone basis relative to the other substeps. Substantially complicated and relatively large equipment is required to perform the amplification step.

The actual hybridization reaction represents the most important and central step in the whole process. The hybridization step involves placing the prepared DNA sample in contact with a specific reporter probe, at a set of optimal conditions for hybridization to occur to the target DNA sequence. Hybridization may be performed in any one of a number of formats. For example, multiple sample nucleic acid hybridization analysis has been conducted on a variety of filter and solid support formats (See G. A. Beltz et al., in *Methods in Enzymology*, Vol. 100, Part B, R. Wu, L. Grossman, K. Moldave, Eds., Academic Press, New York, Chapter 19, pp. 266–308, 1985). One format, the so-called "dot blot" hybridization, involves the non-covalent attachment of target DNAs to filter, which are subsequently hybridized with a radioisotope labeled probe(s). "Dot blot" hybridization gained wide-spread use, and many versions were developed (see M. L. M. Anderson and B. D. Young, in *Nucleic Acid Hybridization—A Practical Approach*, B. D. Hames and S. J. Higgins, Eds., IRL Press, Washington, D.C. Chapter 4, pp. 73–111, 1985). It has been developed for multiple analysis of genomic mutations (D. Nanibhushan and D. Rabin, in EPA 0228075, Jul. 8, 1987) and for the detection of overlapping clones and the construction of genomic maps (G. A. Evans, in U.S. Pat. No. 5,219,726, Jun. 15, 1993).

New techniques are being developed for carrying out multiple sample nucleic acid hybridization analysis on micro-formatted multiplex or matrix devices (e.g., DNA chips) (see M. Barinaga, 253 Science, pp. 1489, 1991; W. Bains, 10 Bio/Technology, pp. 757–758, 1992). These methods usually attach specific DNA sequences to very small specific areas of a solid support, such as micro-wells of a DNA chip. These hybridization formats are micro-scale versions of the conventional "dot blot" and "sandwich" hybridization systems.

The micro-formatted hybridization can be used to carry out "sequencing by hybridization" (SBH) (see M. Barinaga, 253 Science, pp. 1489, 1991; W. Bains, 10 Bio/Technology, pp. 757–758, 1992). SBH makes use of all possible n-nucleotide oligomers (n-mers) to identify n-mers in an unknown DNA sample, which are subsequently aligned by algorithm analysis to produce the DNA sequence (R. Drmanac and R. Crkvenjakov, Yugoslav Patent Application #570/87, 1987; R. Drmanac et al., 4 Genomics, 114, 1989; Strezoska et al., 88 Proc. Natl. Acad. Sci. USA 10089, 1992; and R. Drmanac and R. B. Crkvenjakov, U.S. Pat. No. 5,202,231, Apr. 13, 1993).

There are two formats for carrying out SBH. The first format involves creating an array of all possible n-mers on a support, which is then hybridized with the target sequence. The second format involves attaching the target sequence to a support, which is sequentially probed with all possible n-mers. Both formats have the fundamental problems of direct probe hybridizations and additional difficulties related to multiplex hybridizations.

Southern, United Kingdom Patent Application GB 8810400, 1988; E. M. Southern et al., 13 Genomics 1008, 1992, proposed using the first format to analyze or sequence DNA. Southern identified a known single point mutation using PCR amplified genomic DNA. Southern also described a method for synthesizing an array of oligonucleotides on a solid support for SBH. However, Southern did not address how to achieve optimal stringency condition for each oligonucleotide on an array.

Concurrently, Drmanac et al., 260 Science 1649–1652, 1993, used the second format to sequence several short (116 bp) DNA sequences. Target DNAs were attached to membrane supports ("dot blot" format). Each filter was sequentially hybridized with 272 labeled 10-mer and 11-mer oligonucleotides. A wide range of stringency condition was used to achieve specific hybridization for each n-mer probe; washing times varied from 5 minutes to overnight, and temperatures from 0° C. to 16° C. Most probes required 3 hours of washing at 16° C. The filters had to be exposed for 2 to 18 hours in order to detect hybridization signals. The overall false positive hybridization rate was 5% in spite of the simple target sequences, the reduced set of oligomer probes, and the use of the most stringent conditions available.

A variety of methods exist for detection and analysis of the hybridization events. Depending on the reporter group (fluorophore, enzyme, radioisotope, etc.) used to label the DNA probe, detection and analysis are carried out fluorimetrically, calorimetrically, or by autoradiography. By observing and measuring emitted radiation, such as fluorescent radiation or particle emission, information may be obtained about the hybridization events. Even when detection methods have very high intrinsic sensitivity, detection of hybridization events is difficult because of the background presence of non-specifically bound materials. A number of other factors also reduce the sensitivity and selectivity of DNA hybridization assays.

In conventional fluorimetric detection systems, an excitation energy of one wavelength is delivered to the region of interest and energy of a different wavelength is remitted and detected. Large scale systems, generally those having a region of interest of two millimeters or greater, have been manufactured in which the quality of the overall system is not inherently limited by the size requirements of the optical elements or the ability to place them in optical proximity to the region of interest. However, with small geometries, such as those below 2 millimeters, and especially those on the order of 500 microns or less in size of the region of interest, the conventional approaches to fluorimeter design have proved inadequate. Generally, the excitation and emission optical elements must be placed close to the region of interest. Preferably, a focused spot size is relatively small, often requiring sophisticated optical designs. Further, because it is usually desirable to maximize the detectable area, the size of the optical components required to achieve these goals in relation to their distance from the region of interest becomes important, and in many cases, compromises the performance obtained. Accordingly, a need exists for an improved fluorescent detection system.

Attempts have been made to combine certain processing steps or substeps together. For example, various microrobotic systems have been proposed for preparing arrays of DNA probe on a support material. For example, Beattie et al., in *The 1992 San Diego Conference: Genetic*

*Recognition,* November, 1992, used a microrobotic system to deposit micro-droplets containing specific DNA sequences into individual microfabricated sample wells on a glass substrate.

Various workers have addressed fluid handling in microfluidic and mesoscale devices. A subclass of those efforts involve electronic and/or magnetic forces to aid in the movement of charged materials. For example, Pace U.S. Pat. No. 4,908,112 discloses a generally channel shaped structures containing a plurality of electrodes. Substrates such as silicon are suggested, and an optional covering is suggested for containment. Soane et al. U.S. Pat. No. 5,126,022 discloses a tube like system having a plurality of electrodes by which electrical or magnetic (via current application) fields are generated. Chow et al. (Caliper Technologies) U.S. Pat. No. 5,800,690 discloses a system having a number of fluidic pathways. Finally, Wilding et al. U.S. Patent Nos. 5,304,487 and 5,587,128 describe various channel based systems for mesoscale devices including flow channels, reservoirs and mixing areas.

These and other systems having suffered from various limitations or deficiencies. Generally, the prior devices have been limited in their ability to provide easy fabrication in the z-direction (i.e., perpendicular to the plane of the device). Most microfluidic systems are difficult to scale in the z-direction due to the requirements for fluidic structures such as channels and vias which do not lend themselves to integration in the vertical direction. Generally, the photolithographic and etching techniques used is microengineering are best suited to create essentially planar structures. Yet a further limitation on such systems is the fact that fixed fluidic structures impose limitations on flexibility and functionality.

Generally, the prior art processes have been extremely labor and time intensive. For example, the PCR amplification process is time consuming and adds cost to the diagnostic assay. Multiple steps requiring human intervention either during the process or between processes is suboptimal in that there is a possibility of contamination and operator error. Further, the use of multiple machines or complicated robotic systems for performing the individual processes is often prohibitive except for the largest laboratories, both in terms of the expense and physical space requirements.

As is apparent from the preceding discussion, numerous attempts have been made to provide effective techniques to conduct multi-step, multiplex molecular biological reactions. However, for the reasons stated above, these techniques are "piece-meal" and limited. These various approaches are not easily combined to form a system which can carry out a complete DNA diagnostic assay. Despite the long-recognized need for such a system, no satisfactory solution has been proposed previously.

SUMMARY OF THE INVENTION

Apparatus, methods and modes of operation for a stacked, reconfigurable electronic system for the electrophoretic transport of materials is provided. In one embodiment, a multiple chamber, reconfigurable system is provided. In one implementation, the system includes a first chamber having at least a bottom support and an intermediate support, and a second chamber, said second chamber including a bottom support and a top member, the first and second chambers being coupled through a via. Transport between the first chamber and second chamber may be unidirectional or bidirectional. Various modes of transport may be utilized in conjunction with the electrophoretic transport, such as electrosmotic transport and/or thermal transport. A plurality of individually controllable electrodes are provided within the chambers to permit reconfiguration of the system. A control system is provided for control of said electrodes.

The vias may be controlled by an associated electrode. Preferably, the electrode is formed adjacent, for example, circumferentially surrounding the via. Optionally, an electrode may be disposed within the chamber on a wall opposite from the via, so as to receive a signal generating a repulsive force to the charged materials of interest thereby providing an electrophoretic motion towards the via. The combination of electronic attraction to the via, coupled with electronic repulsion away from the wall opposite the via results in enhanced electrophoretic flow.

The stacked, reconfigurable system is preferably formed from planar, sheet-like materials. For example, the first chamber may be formed from a relatively thin bottom layer and intermediate layer, such as 1 mil Kapton™, while being separated by a spacer having a relatively thicker dimension, e.g., 5 mils. Preferably, the spacer is die-cut so as to form a chamber then formed by the coaction of the bottom layer, intermediate layer and edges of the spacer. Preferably, the spacer is at least five times thicker than the intermediate or bottom layer.

The chambers may include various materials within them. For example, one or more collection electrodes may be disposed within the chambers, optionally near a tap location. Affinity or other filter materials may be included within the chambers. Optionally, a permeation layer may be disposed adjacent any electrode, or within a via, to reduce the damage to biological materials from contact with the electrode.

In yet another aspect of this invention, three or more chambers may be coupled via an electrophoretic buss. The electrophoretic buss comprises a chamber region which spans more than two chambers. Driving electrodes are disposed at substantially opposite ends of the electrophoretic buss. Optionally, an input may be coupled to the electrophoretic buss, which if present, permits use of an electrode through region within the electrode adjacent the input. The electrophoretic buss utilizes the free space nature of the electrophoretic transport, to enhance transport and permit the tapping or selecting removal of materials from the electrophoretic buss. Preferably, collection electrodes are disposed adjacent the periphery of the electrophoretic buss, aiding in the tapping or otherwise removing of material flowing through the electrophoretic buss.

In yet another aspect of this invention, various functions are performed in different chambers, such as at different levels. By segregation of various functions, typically biological processing or analysis functions, processes may be optimized for those functions, resulting in a more focused, sensitive and specific system. In the preferred embodiment, a first chamber is adapted for sample preparation of biological materials. A second chamber is adapted for sorting of the biological materials, which are obtained at least in part from the first chamber. A third chamber is adapted for analysis of the biological materials, which are obtained at least in part from the second chamber. The first, second and third chambers are in fluidic coupling with each other through vias, or by a electrophoretic buss. Optionally, the system includes a chamber adapted for amplification of the biological materials. Optionally, the sample preparation chamber may be disposed central to the device, whereby charged materials of a first state are moved in one direction, and those charged materials of an opposite state are moved in an opposite direction. Additional chambers for the processing of those respective materials are then disposed adjacent the sample preparation chamber on the respective sides.

In yet another aspect of this invention, a system is provided for performing analysis on a pathogen wherein the pathogen is analyzed in a first chamber to determine at least certain information regarding the pathogen, and then transferred to a second chamber, wherein the second chamber is electrically reconfigurable to permit action with respect to a plurality of pathogens, the reconfigurable system being configured at least in part upon the analysis conducted at the first level. By way of example, when analyzing for a biological pathogen, the first level may perform an initial determination broadly as to the type of pathogen, and that information then is used in the configuration of the second chamber for more specific analysis or counteraction with respect to the pathogen. In one embodiment, the response to the pathogen includes a chamber wherein a compound may be synthesized, such as a vaccine or an antidote to the pathogen. In one implementation, that synthesized material is then provided in an injectable structure. Optionally, an air handling system is utilized in conjunction with the pathogen analysis system.

It is therefore an object of this invention to provide for an improved integrated, reconfigurable, multifunctional system.

It is yet a further object of this invention to provide a sensitive, adaptable low-cost diagnostic system.

It is yet a further object of this invention to provide a system having an improved mode of fluidic communication within a multichamber device.

It is yet a further object of this invention to provide a system having improved sensitivity and specificity.

It is yet a further object of this invention to provide systems having dynamic reconfigurable components for the analysis of materials.

DETAILED DESCRIPTION

Figure 1A:
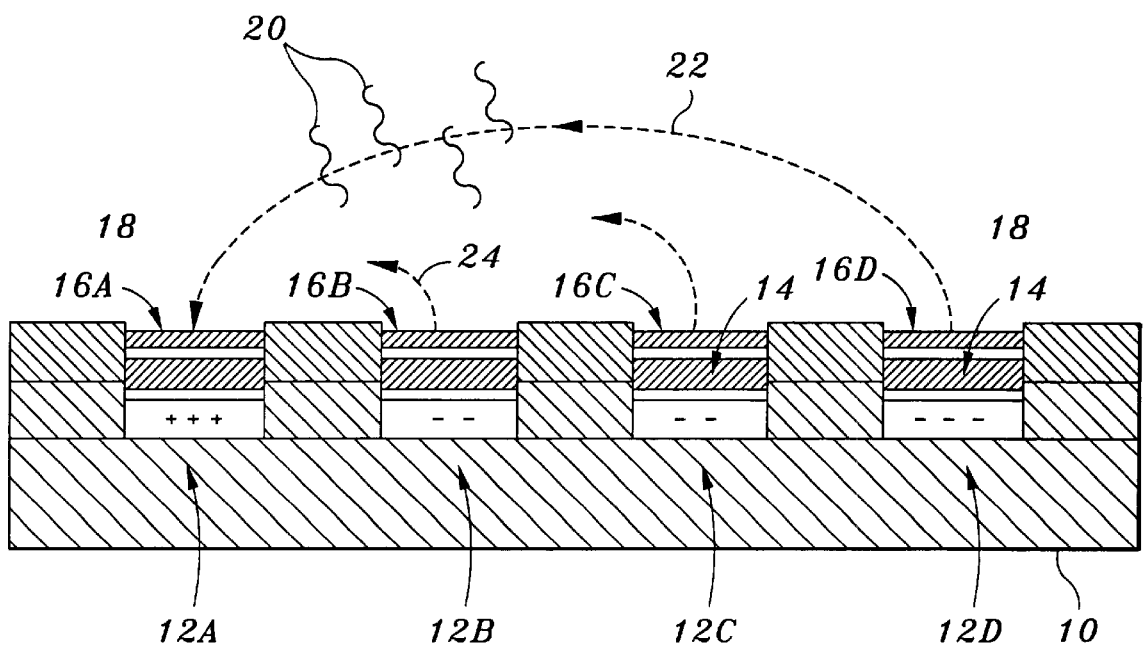
FIGS. 1A and 1B show an active, programmable electronic matrix device (APEX) in cross-section (FIG. 1A) and in perspective view (FIG. 1B).
Figure 1B:
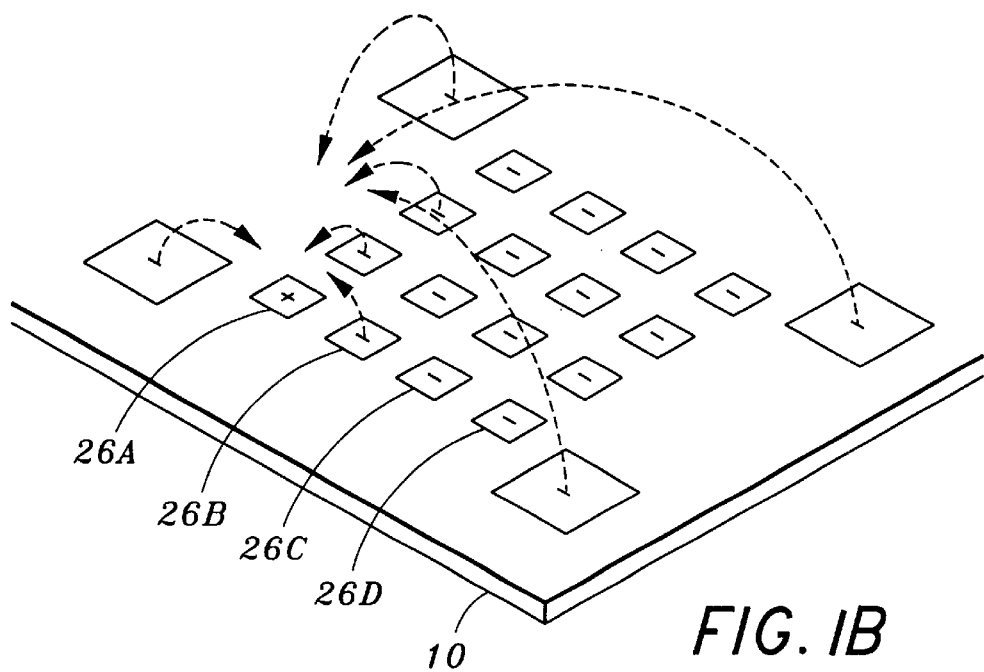

FIGS. 1A and 1B illustrate a simplified version of the active programmable electronic matrix hybridization system for use with this invention. Generally, a substrate 10 supports a matrix or array of electronically addressable microlocations 12. For ease of explanation, the various microlocations in FIG. 1A have been labeled 12A, 12B, 12C and 12D. A permeation layer 14 is disposed above the individual electrodes 12. The permeation layer permits transport of relatively small charged entities through it, but limits the mobility of large charged entities, such as DNA, to keep the large charged entities from easily contacting the electrodes 12 directly during the duration of the test. The permeation layer 14 reduces the electrochemical degradation which would occur in the DNA by direct contact with the electrodes 12, possibility due, in part, to extreme pH resulting from the electrolytic reaction. It further serves to minimize the strong, non-specific adsorption of DNA to electrodes. Attachment regions 16 are disposed upon the permeation layer 14 and provide for specific binding sites for target materials. The attachment regions 16 have been labeled 16A, 16B, 16C and 16D to correspond with the identification of the electrodes 12A–D, respectively.

In operation, reservoir 18 comprises that space above the attachment regions 16 that contains the desired, as well as undesired, materials for detection, analysis or use. Charged entities 20, such as charged DNA are located within the reservoir 18. In one aspect of this invention, the active, programmable, matrix system comprises a method for transporting the charged material 20 to any of the specific microlocations 12. When activated, a microlocation 12 generates the free field electrophoretic transport of any charged functionalized specific binding entity 20 towards the electrode 12. For example, if the electrode 12A were made positive and the electrode 12D negative, electrophoretic lines of force 22 would run between the electrodes 12A and 12D. The lines of electrophoretic force 22 cause transport of charged binding entities 20 that have a net negative charge toward the positive electrode 12A. Charged materials 20 having a net positive charge move under the electrophoretic force toward the negatively charged electrode 12D. When the net negatively charged binding entity 20 that has been functionalized contacts the attachment layer 16A as a result of its movement under the electrophoretic force, the functionalized specific binding entity 20 becomes covalently attached to the attachment layer 16A.

Figure 2:
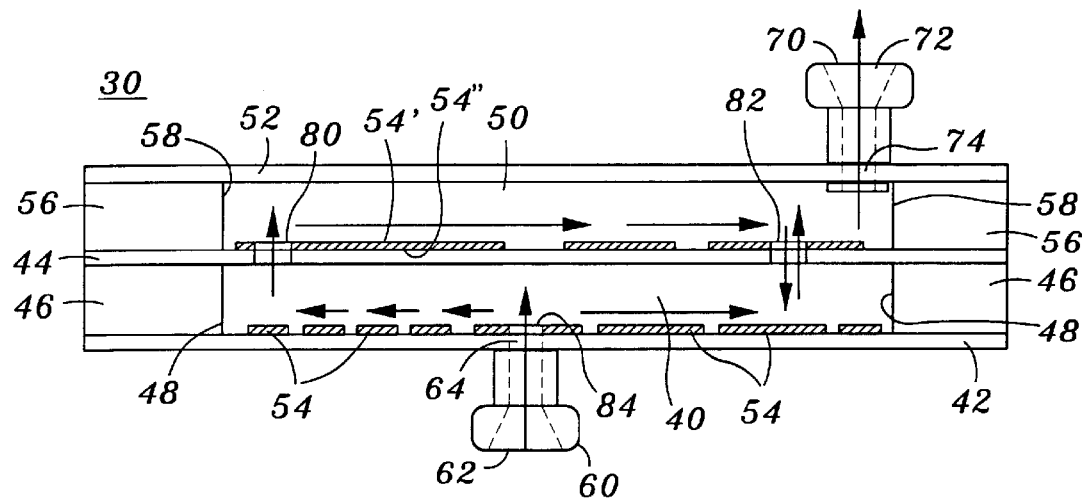
FIG. 2 is a cross-sectional view of a multilayer structure including two chambers and interconnecting vias.

FIG. 2 is a cross-sectional diagram of a laminated, stacked, reconfigurable structure 30 according to one embodiment of this invention. Broadly, the stacked, reconfigurable structure 30 includes a plurality of chambers, in FIG. 2 showing two chambers, a first chamber 40 and a second chamber 50. A chamber comprises a bounded volume for providing controlled flow via electrophoretic, electroosmotic, thermal or other modes of transport, typically having one or more points of connection (e.g., such as by a via or buss) with one or more other chambers. The chamber may be closed except for the presence of vias, and/or a buss, or may have one or more open sides while still defining a volume useable consistent with the goals and objects of this invention.

The first chamber 40 is defined by a bottom support 42, an intermediate member 44 and a spacer 46. The spacer 46 includes edges 48 which provide boundary walls for the first chamber 40 on the left and right ends. The second chamber 50 is defined on the bottom by the intermediate member 44, preferably the same intermediate member 44 which serves to define the top of the first chamber 40. The upper portion of the second chamber 50 is formed by the top member 52, which may optionally be transparent or translucent. Spacer 56 includes edges 58 which serve to define the left and right boundaries of the second chamber 50.

FIG. 2 shows various mechanisms by which the first chamber 40 and second chamber 50 of the stacked, reconfigurable structure 30 interface with the external world and between chambers. An inlet port 60 permits fluidic coupling from external to the device 30 into the first chamber 40 via aperture 64 formed through the bottom support 42. Optionally, the inlet port 60 may include a mating lock 62, such as a Luer lock. The outlet port 70 couples to aperture 74 formed in the top member 52 and provides for (fluidic and possibly gas) output from the stacked, reconfigurable structure 30. While the ports 60, 70 have been labeled inlet and outlet, respectively, they may be reversed without loss of generality. The first chamber 40 and the second chamber 50 are further fluidically (and for gas flow) coupled through the first via 80 and second via 82. The vias 80, 82 are formed through the intermediate member 44, and as shown, through the electrodes 54.

A plurality of electrodes 54 are provided within the reconfigurable structure 30 in shapes and positions to achieve the functionality described herein. Electrodes 54 preferably have a generally sheet-like or planar structure, at least at certain portions of the electrode 54. The electrode 54 includes an upper surface 54' and lower surface 54". In certain of the electrodes, an electrode through region 84 may be located in the electrode 54. In the preferred embodiment, the electrode through region 84 is a hole, that is, the electrode 32 completely circumscribes the electrode through region 84. However, the electrode through region 84 need not be formed as a hole, and may only be bounded by or partially surrounded by the electrode 54, or may be set back from the hole as in an annulus.

This electrode structure is particularly advantageous to aid in the movement, processing and analysis of materials in the system 30. The various vias 80, 82 and apertures 64, 74, preferably have adjacent electrodes 54 formed in the manner described in the preceding paragraph. Such electrodes serve as a conductive structure adapted to receive a signal from a control system or source serving to provide an electromagnetic environment adjacent the through paths through the apertures 64, 74 and vias 80, 82 to control the flow in the manner desired. Optionally, electrodes 54 may be disposed on the chamber 40, 50, in a position opposite to the via 80, 82 or aperture 64, 74.

By way of example, the first via 80 may be disposed opposite an electrode 54 formed on the bottom support 42 directly across from the via 80. Such an electrode may be energized to provide a repulsive force so as to drive materials from the volume of the first chamber 40 towards the first via 80, through and into the second chamber 50. In combination with this repulsive force, the electrode 54 adjacent the left-most electrode through region 84 may be biased attractive to the desired materials to aid in drawing those materials from the first chamber 40 to the second chamber 50.

In this way, the signals provides to the electrodes 54 may generate a reconfigurable flow pattern as required for the operation of the system. FIG. 2 shows arrows depicting possible flow directions. While the first via 80 shows flow from the first chamber 40 to the second chamber 50, the direction of flow may be opposite given appropriate biasing of the electrodes 54. Similarly, the second via 82 is shown having bi-directional arrows. In actual operation, the flow of charged materials may be of but a single direction (e.g., from the second chamber 50 to the first chamber 40) or may indeed be of both directions simultaneously, such as where both positively charged and negatively charged materials are present within the solution contained in the device 30. Such a bi-directional flow may occur in the presence of DNA (negatively charged) and proteins (positively charged).

Thus, the arrows shown in the drawing of FIG. 2 are merely for expository convenience, and not intended to provide a limiting depiction of directionality.

The various structures including the bottom support 42, intermediate member 44, top member 52 and spacers 56 are preferably formed of a sheet-like material. These materials are generally planar, having an upper and a lower surface. Generally, this sheet-like material has lateral extension which is significantly (at least 10:1 times) greater than the thickness of the material. The spacer 46, 56, is preferably formed from a relatively thicker (e.g., 5 mil) sheet-like material. While these thicknesses are currently preferred, the actual thickness may be chosen based upon availability and functional requirements. Preferably the chambers 40, 50 are formed via die cutting of the overall sheet.

The preferred sheet-like material for structures, e.g., the bottom support 42 and spacer 46, is polyimide. One source for sheet polyimide is DuPont who currently sells materials generally ranging from 1 mil to 1.5 mm thick under the trademark Kapton™. Generally, it is desired that these materials have relatively low swelling (preferably less than 10%, more preferably less than 5% and most preferably less than 2%) in the presence of fluids, preferably have relatively low inherent fluorescence, are substantially inert in an acidic environment (most preferably to a pH of 2 and more preferably to a pH of 1), are electrically insulative or nonconducting. Utilizing currently available materials, relatively thin, e.g., 1 mil thickness sheets, may be patterned with 1 mil wide lines and 1 mil wide spaces.

While polyimide is the preferred material, other materials meeting one or more of the criteria include: polymethylmethacrylate (PMMA), polytetrafluorethylene (PTFE-Teflon), polyester (Mylar), polystyrene, polycarbonate and like materials. Further, various layers in the laminated structure 30 may be selected from different materials to optimize the performance of that layer or the laminate structure 30. For example, the exposed surfaces in the chambers 40, 50 may optionally be selected for low adhesion to biological materials. The support may be chosen for its inherent low specific binding with biological materials or the surface may be altered to that purpose. One or more layers may be chosen for high reflectivity, low reflectivity (such as through the use of black or absorbing materials), having a desired texture (e.g., low texture for bonding purposes and surface chemistry optimization), or have hydrophobic or hydrophilic properties. Preferably, the layers are nonporous. The laminated structure 30 is generally preferred to be impermeable to fluids, such as water.

The electrodes 54 are preferably formed on or integral to a sheet, such as a polyimide sheet. The electrode materials are preferably noble metals, most preferably gold. Generally, it is preferred that no base metals which would adversely affect biological materials to be supplied to the laminated structure 30, such as DNA, are exposed in the electrode 54. Most preferably, it is desirable to avoid copper and iron, and to a lesser extent lead and tin in the materials, or at least, avoiding the exposure of those materials or their ions if present to the biological materials. The electrode 30 should be formed from a material, and result in a structure, which is generally noncorrosive, is bondable, adheres to other materials, serves to minimize or avoid leakage currents, generates relatively low amounts of electrochemistry and has a relatively high electrochemical voltage at which the surface of the electrode emits constituents materials. Other desirable electrodes may be formed from nichrome, platinum, nickel, stainless steel or indium tin oxide (ITO), ITO being advantageously used when optical detection, especially from the back side, is utilized.

In the preferred embodiment, when polyimide sheets are utilized, the preferred adhesive is DuPont acrylic adhesive, or polyester adhesive. Generally, it is desirable that the adhesive have low squeeze out properties such that during the lamination process, excessive amounts of adhesive do not exit such as at the interior edge 48, 58, lest excessive, and unpredictable, amounts of adhesive reside on the electrode 54. Generally, the adhesive is on the order of 1 mil thick.

The laminated structures are preferably formed by methods which permit the high yield, low cost manufacturing of high quality devices. The various holes, such as vent holes, sample through holes and electrode through regions may be formed through any known technique consistent with the objects and goals of this invention. For example, microminiaturized drills may form holes as small as 3–8 mils, while laser drilled holes may be as small as 4 mils, or photolithographically patterned holes may be formed to substantially 1 mil. Generally, utilizing current technology, the thinnest sheets permit the formation of the smallest diameter holes. Optionally, chemical etching may be utilized to remove debris from the holes. This technique is particularly advantageous after laser drilling of holes, so as to reduce or remove previously ablated materials. After the electrodes are patterned on the support, and various layers are fabricated, the laminated or composite structure 30 is adhered together. Generally, it is desirable to have minimal or no squeeze out of adhesive to avoid nonuniformity in terms of exposed electrode area. In one embodiment, relatively larger holes are first formed, and then relatively smaller holes are drilled through the larger holes. Alternately, the supports including vents and holes may be formed first, and then aligned, such as through optical alignment, prior to the setting of the adhesive.

The electrodes in the various embodiments may optionally be in contact with or adjacent to a permeation layer. Generally, the permeation layer serves as a medium to prevent or reduce the amount of sample which may directly contact the electrode surface. Various permeation layers include polymer coatings, or other materials compatible with these goals and objects. In yet another structure configuration, a polymer layer or permeation layer may be disposed within a via or electrophoretic buss. Such a structure may form essentially a miniature separation column to provide separation, for example, of such species as DNA and proteins.

Yet other regions of the device may be decorated with affinity materials. For example, the transport of charged polymers or ions through the vias could be used to form purification by separation on the basis of charged-to-mass ratio or attraction to an affinity matrix which could be coated onto or near an electrode, in the via or electrophoretic buss. In yet another aspect, small charged species may be separated from macromolecules by using molecular weight cut-off membranes. Such membranes may be located in the vias or in the electrophoretic buss. Yet further structures for assays or functional analysis may be performed by including functional groups corresponding to said assays or analysis in the coating on the electrodes. For example, DNA probes or antibodies may be attached to the permeation layers which are in turn attached to or adjacent the electrodes.

Figure 3:
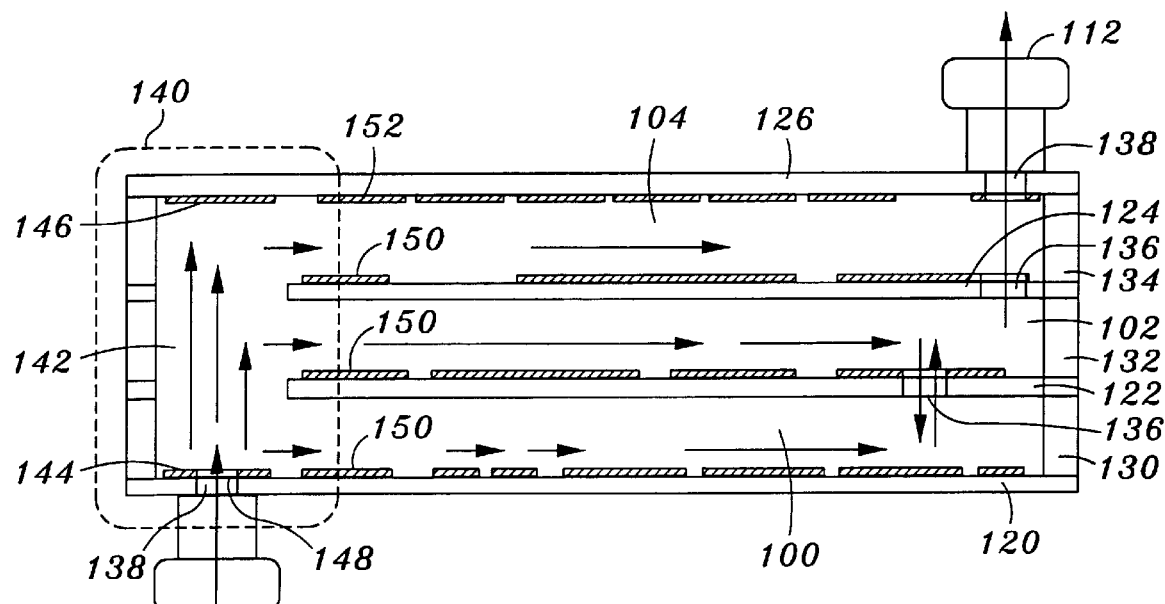
FIG. 3 is a cross-sectional view of a multilayer structure including at least three chambers, multiple vias and an electrophoretic buss.

FIG. 3 is a cross-sectional view of a multichamber system. Here, a first chamber 100, second chamber 102 and third chamber 104 are stacked one on top of the other. Structurally similar features between FIG. 3 and FIG. 2 are present, and the comments regarding one figure apply with equal force with respect to other figures. Thus, an inlet port 110 and an outlet port 112 each include an aperture which provides for fluidic (and possibly gas) communication from external of the device to the various interior portions. The device itself is preferably fabricated with stacked laminates, such that from the bottom to the top the system would include a bottom support 120, a first intermediate support 122, a second intermediate support 124 and a top member 126. These structures are separated by the presence of a first spacer 130, second spacer 132 and third spacer 134. The spacers 130, 132 and 134 are preferably relatively thick (e.g., five times thicker, and more preferably substantially ten times thicker) than the thickness of the other support members 120, 122, 124 and 126. It will be appreciated that all support members need not be of a uniform thickness (and therefore chambers 100, 102, 104 of uniform volume), but may be varied as desired to serve the required functionalities. Vias 136 are located between the first chamber 100 and second chamber 102, and between the second chamber 102 and third chamber 104. Apertures 138 coupled to the ports 110, 112 so to provide coupling between external to the device and internal to the device. As shown, outlet port 112 is optionally disposed at a portion of the third chamber 104 which is away from the electrophoretic buss 140, to thereby induce flow through said third chamber 104.

An electrophoretic buss 140 typically consists of a chamber region 142 which spans more than two chambers 100, 102, 104. Driving electrodes 144, 146 are disposed at substantially opposite ends of the electrophoretic buss 140. Driving electrode 144 disposed on the bottom support 120 preferably includes an electrode through region 148 adjacent the aperture 138 whereby flow through the surrounding electrode 144 may be effected. The driving electrode 146 disposed on the top member 126 may be uniform or may include an electrode through region if necessary to promote fluidic or gas transfer through the region containing the driving electrode 146. The electrophoretic buss 140 serves to provide a volume in which the free space nature of the electrophoretic transport in the device may permit the easy transport of materials to the desired chamber 100, 102, 104. Preferably, collection electrodes 150 are disposed adjacent the periphery of the electrophoretic buss, aiding in the tapping or otherwise removing of the material flowing through the electrophoretic buss 140 into the chamber (e.g., chamber 104). Optionally, upper electrodes 152 may be disposed within the chambers 100, 102, 104 to aid in the tapping or movement of materials. By activation of the collection electrodes 150, and optionally the upper electrodes 152, materials may be removed from the electrophoretic buss 140 at the time when desired materials are in proximity thereto. In the structure of FIG. 3, the "tap" consists of selecting material from the electrophoretic buss 140 having a first direction flow into a flow direction which is substantially perpendicular thereto, namely, into and through a chamber 100, 102, 104.

Figure 4A:
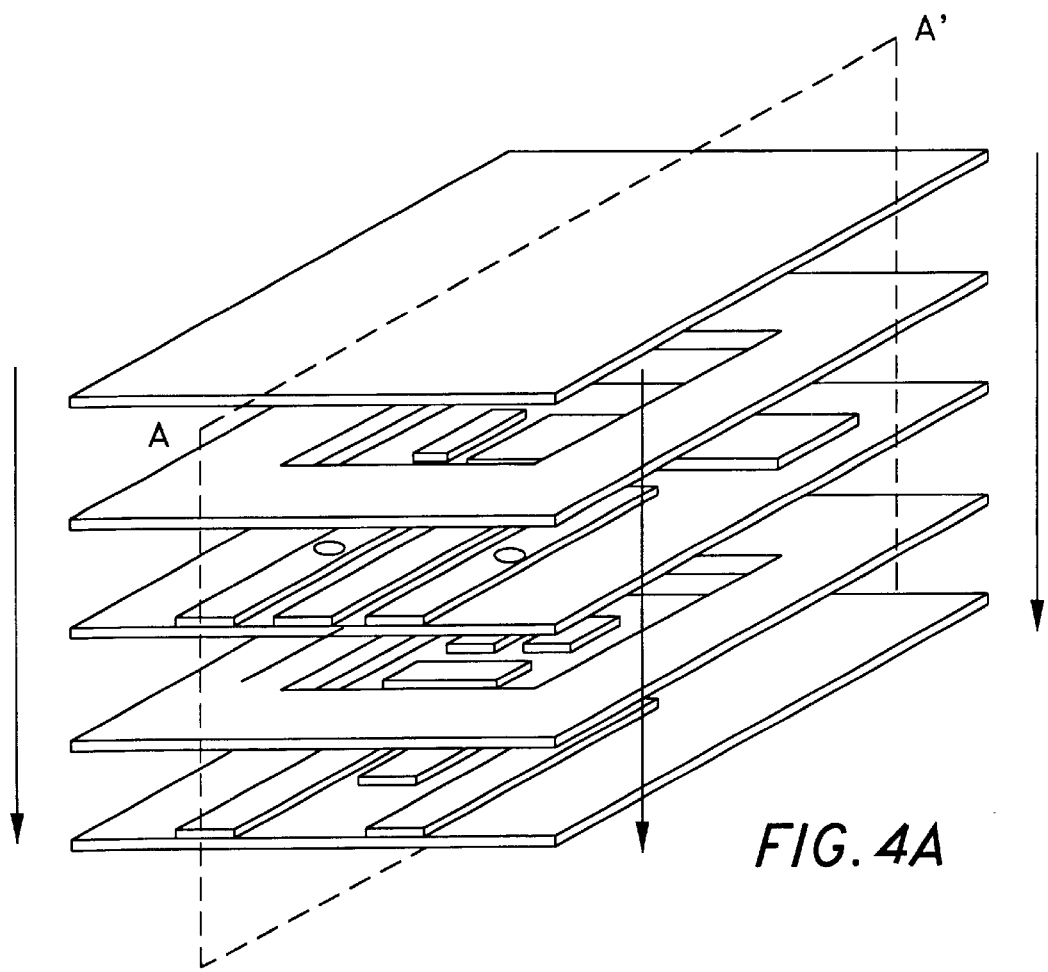
FIGS. 4A and 4B show a multilevel, stacked, reconfigurable system for transport and analysis of charged materials in perspective view (FIG. 4A) and in cross-section (FIG. 4B).
Figure 4B:
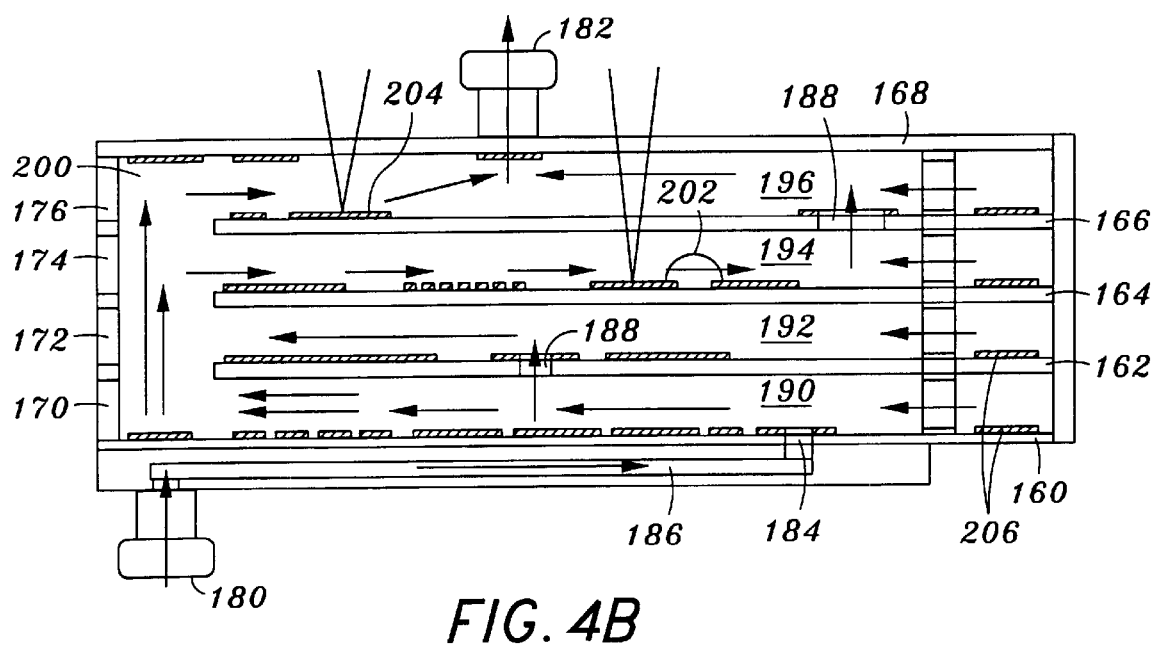

FIGS. 4A and 4B show perspective and cross-sectional (along the plane A–A') of a full stacked assay system. The structures having similarity to those described in the preceding figures apply with equal force here. The relatively thin base layer 160, first intermediate layer 162, second intermediate layer 164, third intermediate layer 166 and tap number 168 are separated by the series of first spacer 170, second spacer 172, third spacer 174 and fourth spacer 176. An input port 180 is connected to an aperture 184 in the base layer 160 by an optional pathway 186. The output port 182 is coupled through the top member 168. One or more vias 188 may be included.

In one aspect of this invention, the various chambers may have different principle functionalities. For example, first chamber 190 may be principally for sample preparation, such as through filtering, affinity membranes and dilution. Further, the first chamber 190 may include a sorting level, such as through the use of dielectrophoresis for cell sorting and initial screening. At least some of the materials from the first chamber 190, such as DNA obtained from the cell sorting and initial screening is provided via the electrophoretic buss 200 or vias 188 to other chambers or levels. For example, at least a portion of the output of the first chamber 190 may be transported through via 188 into the second chamber 192 wherein DNA amplification (e.g., PCR, SDA, enzymatic amplification, or other linear or exponential amplification technique) may be utilized. The third chamber 194 may provide functions such as DNA assay. Optionally, the assay may be performed on an assay chip 202, the output of which passes through via 188 to the fourth chamber 196. The fourth chamber 196 may optionally perform other, different, processes or analysis, such as an immunoassay at assay site 204.

Optionally, detection of the conditions at the assay chips 202 and/or the assay site 204 may be performed optically, in which case it is desirable to have optical access through the top member 168, and as necessary, through other intermediate support layers, such as the third intermediate layer 166. Various detection systems may be utilized, including systems disclosed in "Scanning Optical Detection System", filed May 1, 1997, published as PCT US98/08370 U.S. Ser. No. 08/846,876, incorporated herein by reference. Optionally, the various assay chips 202 or assay sites 204 may be formed on chips, such as silicon chip based technology (See, e.g., FIG. 1), and may optionally be mounted on the intermediate support layers 162, 164, 166 through various attachment technologies, such as flip-chip attachment techniques. Heaters/electrodes 206 are disposed at the right most portion of the chambers 190, 192, 194 and 196, and may comprise reagent delivery regions.

With respect to the structures of FIGS. 2, 3, 4A and 4B, described above, it will be appreciated that alternative terminology may be utilized to describe structural or functional attributes. For example, the lowest intermediate support (intermediate member 44 in FIG. 2, first intermediate support 122 in FIG. 3, and first intermediate layer 162 in FIGS. 4A and 4B) could also be referred to as a top member for the first chamber as it is disposed above the chamber space and bottom. Likewise, that same structure could also be termed the base layer or bottom support or like terminology when used in context of the next higher chamber. Stated otherwise, the first intermediate support 122 of FIG. 3 may be both termed a top member for the first chamber 100 as well as the bottom support or base layer for the second chamber 102.

Figure 5:
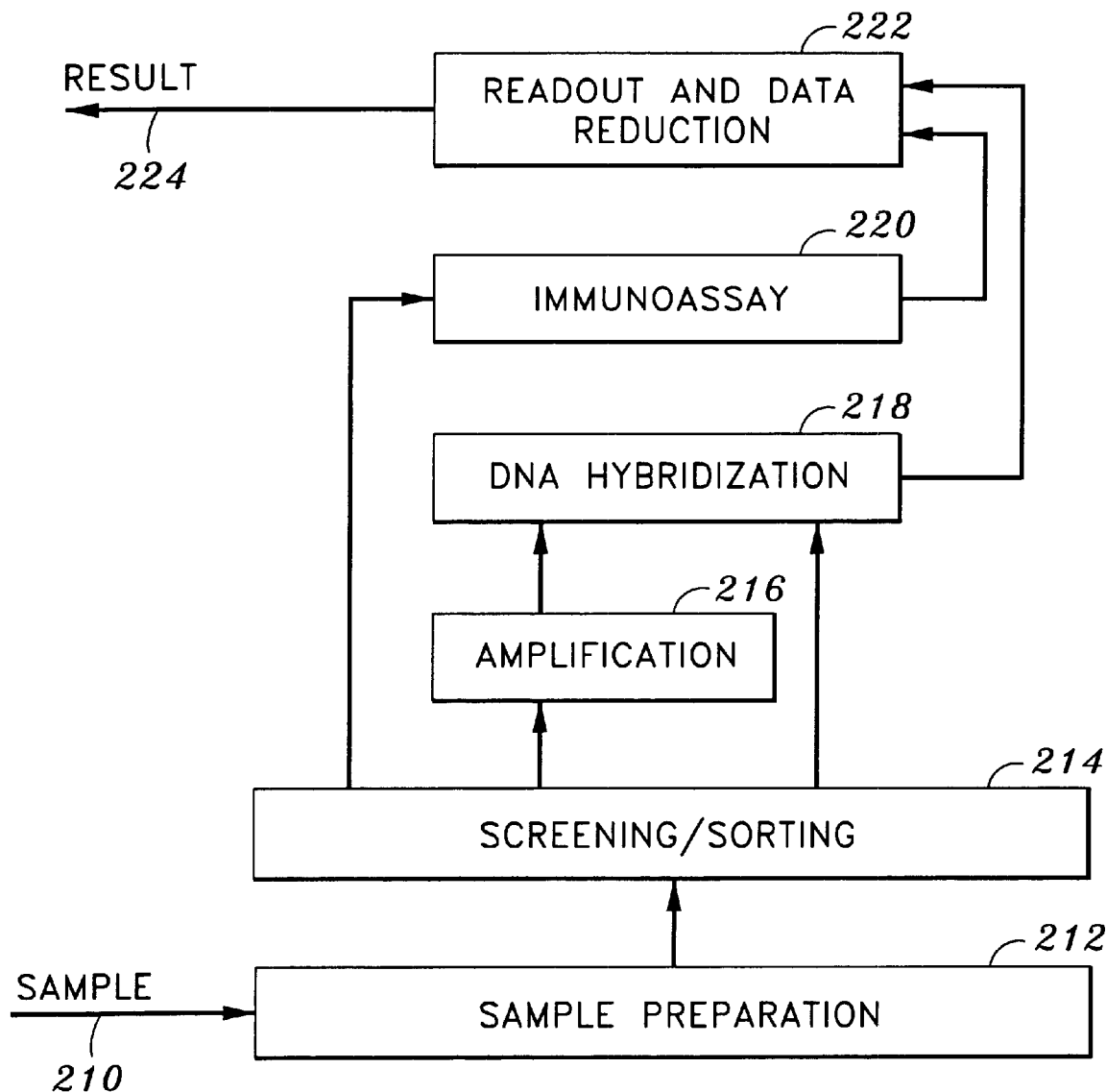
FIG. 5 is a flowchart showing steps from the receipt of a sample through to the result of the intervening action steps.

FIG. 5 shows a flow chart of a structure and implementation such as in FIGS. 4A and 4B. The description will compare the functional steps of the flow chart of FIG. 5 with the structure shown in FIGS. 4A and 4B. Sample 210 is provided to sample preparation region 212 from input port 180 to first chamber 190 wherein the screening/sorting 214 occurs. Optionally, amplification 216 may occur if transfer through via 188 into the second chamber 192 is effected. Otherwise, the screening/sorting step 214 leads to DNA hybridization 218 via the electrophoretic buss 200, as is the case with the output of the amplification step 216 from the second chamber 192. Some or all of the output of the screening/sorting step 214 may be supplied to the immunoassay step 220 such as from the output of the first chamber 190 via the electrophoretic buss 200 to the fourth chamber 196. DNA hybridization 218 may occur in the third chamber 194, which may be reached via the electrophoretic buss 200. Monitoring of the output of the system, such as through optical monitoring of the assay site 204 and assay chips 202 results in read out and data reduction 222. From this, the result 224 is obtained.

Figure 6:
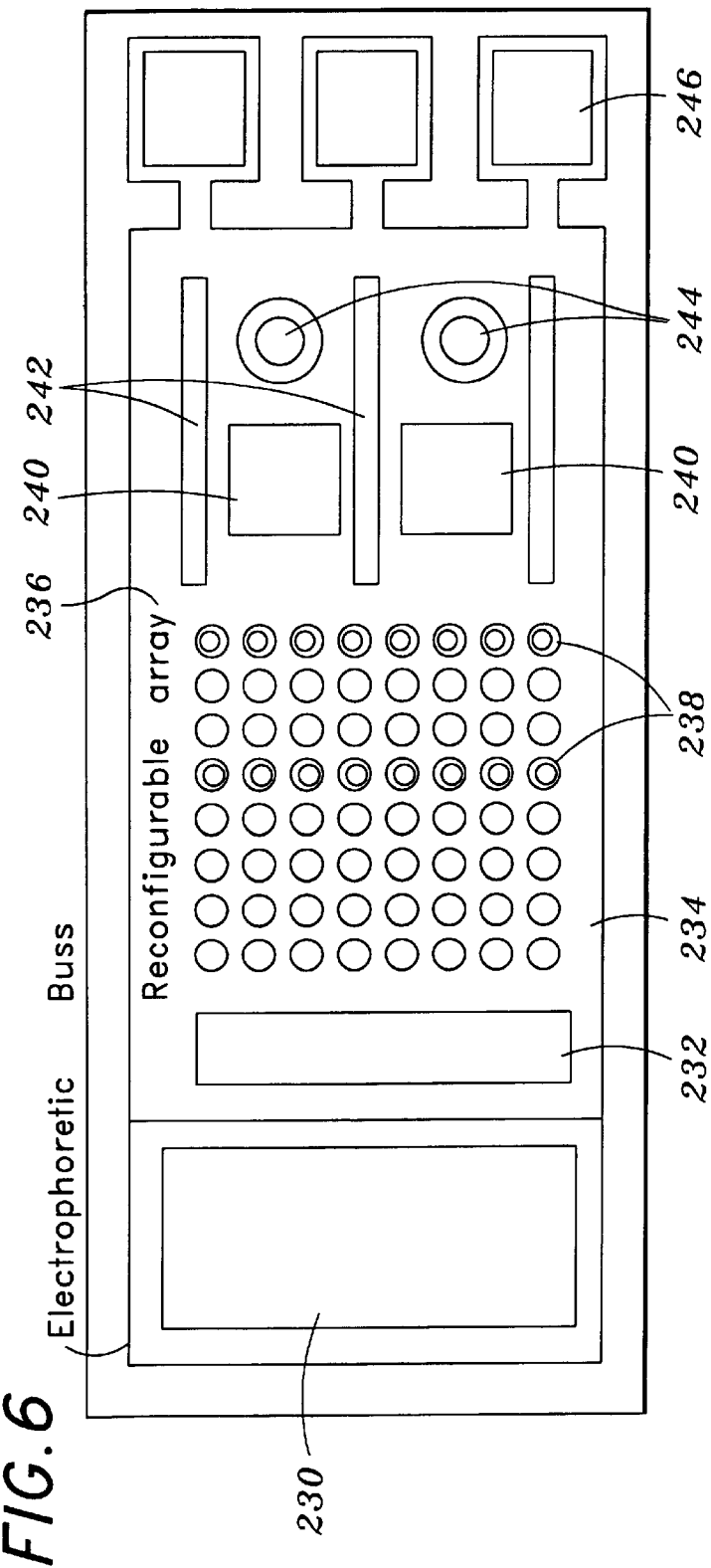
FIG. 6 is a plan view of an assay level in a multilevel, reconfigurable system including an electrophoretic buss and multiple reagent dispensers.

FIG. 6 is a plan view from the top of the assay level (e.g., the third chamber 194 in FIG. 4B). The electrophoretic buss 230 is disposed to the left of the structure. A collection electrode 232 is preferably disposed on the substrate 234 to aid in the removal or tapping of materials to the electrophoretic buss 230. Reconfigurable array 236 is shown as an 8×8 array of sites, though the number may be larger or smaller as required. Two columns of vias 238 may be selectively utilized for transportation between various levels. Assay chips 240 are then disposed to the right of the reconfigurable array 236. Optionally, focusing electrodes 242 may be disposed adjacent the assay chips 240. (See, e.g., Ser. No. 09/026,618, entitled "Advanced Active Electronic Devices for Molecular Biological Analysis and Diagnostics and Methods for Manufacture of Same", filed Feb. 20, 1998, incorporated herein by reference as if fully set forth herein, specifically with respect to focusing electrode designs.) Additional vias 244 provide for fluidic or gas transport between various levels. Reagent containers 246 are fluidically coupled to the remainder of the chamber to the left.

Figure 7:
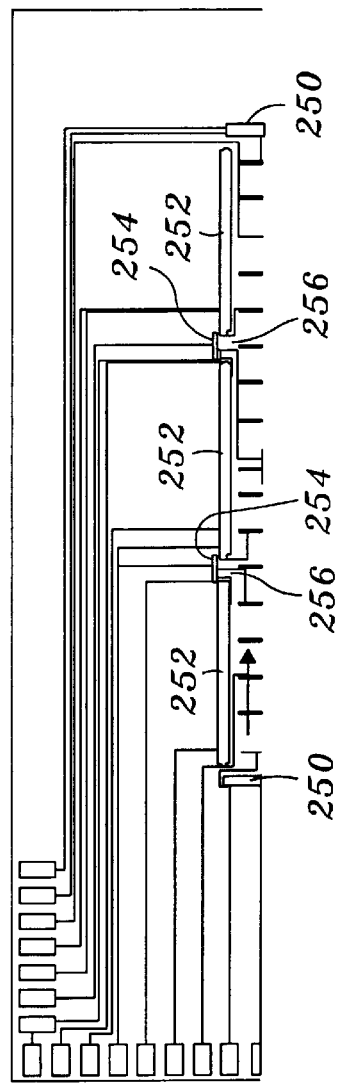
FIG. 7 is a plan view of an electrode configuration including one embodiment having taps from a principle transport pathway.

FIG. 7 is a plan view of an electrode configuration for electrophoretic free field transport including electronic taps. Driving electrodes 250 provide for a net overall electrophoretic force in the direction of the arrow. Focusing electrodes 252 serve to provide a constraining force for charged materials in the direction of the flow represented by the arrow. A tap electrode 254 is disposed above the gap 256 formed by separation between adjacent focusing electrodes 252. In operation, materials being electrophoretically transported between the driving electrodes 250 may be cause to move with a force component in a direction transverse to the line between the driving electrodes 250, towards the cap electrodes 254.

The systems described herein have numerous applications. Without limiting the generality of the foregoing description, various particularly advantageous applications will be described herein.

Turning now to the operation of the systems described, above, in typical operation, the fluidic system would first be filled with an appropriate buffer. Next, the sample of interest would be injected into the input port. By selective activation of the electrodes, the desired materials would be attracted to the input electrodes. Damages to the sample may be avoided if a permeation layer is utilized, so as to prevent the unimpeded, direct contact of the materials with the electrode. The charged species then moves between electrodes in the planes of the structure to perform various functions. For biological samples, these functions may include some or all of the following: cell sorting, such as by dielectrophoresis, electronic lysis, and extraction of DNA, RNA or proteins from the lysed cells, electric-field driven amplification, sequence enrichment by hybridization, hybridization assays, protein binding assays, chemical sample processing, including mixing and synthesis steps. After processing is completed in the initial level, the appropriate species may then be transported through vias or the electrophoretic buss to the next or higher level in the stack. This is also optionally achieved electrophoretically by biasing an electrode below the vias so as to repel the species of interest and by biasing the ring electrode above the via so as to attract the species. In this way, chemical species may be mapped from one level to the next level. Sample preparation may advantageously be performed in an intermediate or middle level. This is so since proteins (typically having a positive charge) will move in an opposite direction to DNA (typically having a negative charge) to promote efficient separation.

In operation, it may be highly advantageous to separate or allocate various biological or chemical functions to distinctly different levels or chambers. By creating a layered system, it is possible to segregate various biochemical functions to different layers so as to optimize the electrical and chemical environments and to perform the series of operations necessary to produce a meaningful identification of viral, bacterial, and toxic agents. By way of example, if an initial layer includes the sample preparation functions, that layer may be used to filter out extraneous material from the target sample. Filters and affinity membranes may be utilized, among other structures, to clean the sample at an initial, e.g., crude, level. A next level may utilize sorting an screening for pathogenic cells. At such a level, optionally, dielectrophoresis may be utilized to perform cell sorting and electronic cell lysis to extract DNA and target proteins from the crude sample. After cell lysis, the released DNA, charged chemical and biological toxins, and other molecules of interest may be transported electrophoretically to a series of diagnostic levels. Some DNA may be directed to an amplification level through appropriate vias, while proteins of interest could be moved to the electrophoretic buss where the larger potentially available currents may results in more rapid movement of the proteins. Since proteins usually move more slowly than DNA, the proteins final destination will depend in part on the time of flight actuation of collection electrodes on the appropriate levels.

In yet another aspect of this device, the system may be reconfigured as a result of an initial analysis on a sample. Thus, the stacked system may perform directed assays, that is, where the system may sort cells, screen for pathogens and then perform specialized analysis on reconfigurable arrays based on the screening information. Significant improvements in both the speed and accuracy result for multiplexed tests. Furthermore, different kinds of biochemical information relating to DNA sequence and toxin repertoire may be collected from specific microorganisms, helping to identify the threat and select appropriate countermeasures. By electronically configuring the assay arrays based upon initial analysis, sensitivity may be optimized for the appropriate DNA sequence and antigens present at those locations. The assay process would be streamlined, also resulting in a significant enhancement of sensitivity and specificity by choosing appropriate probe sets and redundancy from a large array of available microlocations.

In yet another aspect of this system, the electronic tap may be used to selectively remove material from one region of transport, to yet another region or chamber. Optionally, a second power supply may be utilized so as to effect a lateral force vector on the ions of interest, as supplied from an electrode coupled to the second power supply. Optionally, an electronic gate may be utilized to regulate the flow of ionic species between chambers or levels. For example, a mesh electrode may be placed between the driving electrodes 144, 146 (FIG. 3) or at or in vias 188.

In yet another application, drug discovery may be performed through the synthesis of various products which are then mapped to potential binding sites. Synthesis products, e.g., peptides, may be mapped to potential binding sites for drug discovery. The use of an array of electrodes and vias to map the products of a number of synthesis reactions performed on a first level on to an array of analysis sites on another (second) level may be utilized.

Considering the synthesis reaction in more detail, the system is able to concentrate reagents to enhance the reaction kinetics, create pH gradients at the electrodes under bias which can be utilized to deprotect various reaction groups, and move in reactive groups with good control of their type and quantity to precisely control microchemical reactions. This sort of reaction control could, for example, be used to synthesize oligonucleotides and oligopeptides. For oligopeptide synthesis, a strategy could be employed that utilizes amino acid building blocks with fMoc protecting groups which are also acid labile. In addition, the permeation layer would contain amino groups blocked with acid labile tBOC groups. Selective deprotection of sites and attachment would be accomplished using acid cleavage to expose hydroxyl groups. To allow attachment at a specific site, the electrode benefit it would be positively biased at a sufficient potential or current to create acidic conditions. At the appropriate current level our data shows that the low pH is limited to a region near the activated electrode, so cross-talk between microlocations is minimized and specific control of the synthesis at individual reaction sites can be achieved. A variety of chemical ligation procedures are available for peptide assembly. These reactions may be made both highly concentration dependent and highly pH dependent, two parameters which may be programmed and carefully controlled using the disclosed (and incorporated) electrode technology. Rapid combinatorial assembly of preformed peptide epitope building blocks can be achieved. Linkage will be designed to take advantage of electric field mediated concentration and acidification which occurs over positively biased electrodes on the chip.

In yet another application, medical diagnostic assays may be performed. By segregation of various functionalities to different levels, the speed and precision of operation of the system may be enhanced.

In yet another application, the system may be utilized in the detection of pathogens, such as may occur in biological warfare applications. The stacked, reconfigurable system may perform directed assays, such as to sort cells, screen for pathogens, and then perform specialized assays on reconfigurable arrays based on the screening information. This selection and specialization of the arrays results in significant improvements in both the speed and the accuracy of the multiplexed tests. The different kinds of biochemical information relating to DNA sequence and toxin repertoire can be collected from specific microorganisms, helping to identify the threat and select appropriate counter measures. In yet a further optional aspect, the system may be adapted to generate the counter measures. For example, based upon the initial assay or other analysis, it is possible to perform directed peptide synthesis which results in the on-chip synthesis of vaccines to respond to the biological threats. Optionally, a detachable support may be anchored over one or more electrodes which may be used as the starting material for linkage of peptides. The resulting synthetic peptide may be used as a vaccine, or for drug synthesis. Optionally, the peptides may be anchored to the detachable support, which may be removed from the chip for injection. For use as a drug, for example, to block binding of a neurotoxin, the peptides may be attached to a cleavable linker such as a disulfide.

Optionally, such a detection system may be modified to detect airborne pathogens. Advanced sample collection techniques including air handling and sampling techniques may be utilized. To capture the airborne pathogens when admixed with significant amounts of spurious background material, an optional pre-filtering step may be utilized to minimize the volume of background material relative to the pathogens. In one implementation, electrostatic methods may be utilized for particulate attraction, which may then be utilized in conjunction with the electrophoretic techniques described herein to separate species according to their charge.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

What is claimed is:

1. A stacked, reconfigurable system for performing analysis on a pathogen, the system comprising:

an inlet for receipt of a sample including said pathogen, a first chamber defined by a bottom support, an intermediate member, and a first spacer, said first chamber being coupled to said inlet through the bottom support, said first chamber including an analysis system, said analysis system including electrodes for the electrophoretic transport of said pathogen, and an analysis system for determining at least certain information regarding said pathogen, a second chamber stacked on top of said first chamber, said second chamber defined by the intermediate member, a top member, and a second spacer, said second chamber being in fluid communication with said first chamber through at least one via formed in the intermediate member, said second chamber being electrically reconfigurable to permit synthesis of a compound, wherein the reconfigurable system is configured based at least in part upon the analysis in said first chamber, and a detachable support disposed in the second chamber, wherein the synthesized compound is anchored to the detachable support, the detachable support being removable from the system and used for injection.

2. A stacked, reconfigurable detection and analysis apparatus comprising:

an inlet for receipt of a sample containing charged biological materials;

a first chamber defined by a bottom support, an intermediate member, and a first spacer, said first chamber being coupled to said inlet through the bottom support, said first chamber including an analysis system, said analysis system including electrodes for the electrical transport and screening of the charged biological materials; and a second chamber stacked on top of said first chamber, said second chamber defined by the intermediate member, a top member, and a second spacer, said second chamber being in fluid communication with said first chamber through at least one via formed in the intermediate member, the second chamber including one or more electrically reconfigurable arrays disposed therein, the one or more electrically reconfigurable arrays being electrically reconfigurable to perform directed peptide synthesis based the screening of the charged biological materials.

3. A stacked, reconfigurable detection and analysis apparatus comprising:

an inlet for receipt of a sample containing charged biological materials;

a first chamber defined by a bottom support, an intermediate member, and a first spacer, said first chamber being coupled to said inlet through the bottom support, said first chamber including an analysis system, said analysis system including electrodes for the electrical transport and screening of the charged biological materials; and a second chamber stacked on top of said first chamber, said second chamber defined by the intermediate member, a top member, and a second spacer, said second chamber being in fluid communication with said first chamber through at least one via formed in the intermediate member, the second chamber including one or more electrically reconfigurable arrays disposed therein, the one or more electrically reconfigurable arrays being electrically reconfigurable to synthesize a compound based the screening of the charged biological materials, the second chamber including a detachable support disposed therein, wherein the synthesized compound is anchored to the detachable support, the detachable support being removable from the system and used for injection.

4. A method for performing analysis on charged biological materials comprising the steps of:

delivering an airborne sample containing charged biological materials to a first chamber;

transporting and screening the charged biological materials within the first chamber;

transporting one or more species contained within the charged biological materials to a second chamber; and performing one or more specialized assays on the one or more species contained within the second chamber using at least one reconfigurable array, the reconfigurable array being configured based on information obtained from the screening of charged biological materials in said first chamber.

5. The method of claim 4, further comprising the step of pre-filtering the airborne sample containing charged biological materials.

6. A method for performing analysis on charged biological materials comprising the steps of:

delivering a sample containing charged biological materials to a first chamber defined by a bottom support, an intermediate member, and a first spacer;

screening the charged biological materials within the first chamber;

transporting one or more species contained within the charged biological materials to a second chamber stacked on top of said first chamber, said second chamber defined by the intermediate member, a top member, and a second spacer, said one or more species entering said second chamber through at least one via formed in the intermediate member;

performing one or more specialized assays on the one or more species contained within the second chamber using at least one electrically reconfigurable array, the electrically reconfigurable array being configured based on information obtained from the screening of charged biological materials in said first chamber; and synthesizing a compound in said second chamber, wherein the compound is anchored to a detachable support provided in the second chamber.

7. A method for performing analysis on charged biological materials comprising the steps of:

delivering a sample containing charged biological materials to a first chamber defined by a bottom support, an intermediate member, and a first spacer;

screening the charged biological materials within the first chamber;

transporting one or more species contained within the charged biological materials to a second chamber stacked on top of said first chamber, said second chamber defined by the intermediate member, a top member, and a second spacer, said one or more species entering said second chamber through at least one via formed in the intermediate member;

performing one or more specialized assays on the one or more species contained within the second chamber using at least one electrically reconfigurable array, the electrically reconfigurable array being configured based on information obtained from the screening of charged biological materials in said first chamber; and synthesizing a peptide in said second chamber.

8. A stacked, reconfigurable system for performing analysis on a pathogen, the system comprising:

an inlet for receipt of a sample including said pathogen, a first chamber defined by a bottom support, an intermediate member, and a first spacer, said first chamber being coupled to said inlet through the bottom support, said first chamber including an analysis system, said analysis system including electrodes for the electrophoretic transport of said pathogen, and an analysis system for determining at least certain information regarding said pathogen, a second chamber stacked on top of said first chamber, said second chamber defined by the intermediate member, a top member, and a second spacer, said second chamber being in fluid communication with said first chamber through at least one via formed in the intermediate member, said second chamber being electrically reconfigurable to permit action with respect to a plurality of pathogens, wherein the reconfigurable system is configured based at least in part upon the analysis in said first chamber, and an air handling system comprising an electrostatic generator coupled to the inlet.

9. A stacked, reconfigurable detection and analysis apparatus comprising:

an inlet for receipt of a sample containing charged biological materials;

a first chamber defined by a bottom support, an intermediate member, and a first spacer, said first chamber being coupled to said inlet through the bottom support, said first chamber including an analysis system, said analysis system including electrodes for the electrical transport and screening of the charged biological materials;

a second chamber stacked on top of said first chamber, said second chamber defined by the intermediate member, a top member, and a second spacer, said second chamber being in fluid communication with said first chamber through at least one via formed in the intermediate member, the second chamber including one or more electrically reconfigurable arrays disposed therein, the one or more electrically reconfigurable arrays being electrically reconfigurable to perform specialized analysis based the screening of the charged biological materials; and an air handling system comprising an electrostatic generator coupled to the inlet.

\* \* \* \* \*